US006846842B2

(12) United States Patent
Ajami et al.

(10) Patent No.: US 6,846,842 B2
(45) Date of Patent: Jan. 25, 2005

(54) PYRUVATE ESTER COMPOSITION AND METHOD OF USE FOR RESUSCITATION AFTER EVENTS OF ISCHEMIA AND REPERFUSION

(75) Inventors: Alfred M. Ajami, Brookline, MA (US); Carrie A. Sims, Boston, MA (US); Mitchell P. Fink, Pittsburgh, PA (US)

(73) Assignees: Beth Israel Deconess Medical Center, Inc., Boston, MA (US); Xanthus Life Sciences, Inc., Montreal (CA)

( * ) Notice: Subject to any disclaimer, the term of this patent is extended or adjusted under 35 U.S.C. 154(b) by 0 days.

(21) Appl. No.: 10/116,707

(22) Filed: Apr. 4, 2002

(65) Prior Publication Data

US 2003/0073743 A1 Apr. 17, 2003

Related U.S. Application Data

(63) Continuation of application No. PCT/US00/27758, filed on Oct. 6, 2000.
(60) Provisional application No. 60/158,091, filed on Oct. 7, 1999.

(51) Int. Cl.$^7$ .................. A61K 31/231; A61K 31/19
(52) U.S. Cl. ......................... 514/547; 514/557
(58) Field of Search ............... 514/533, 921, 514/547, 557

(56) References Cited

U.S. PATENT DOCUMENTS

| | | |
|---|---|---|
| 3,920,835 A | 11/1975 | Van Scott et al. |
| 3,984,556 A | 10/1976 | Hardtmann |
| 3,988,470 A | 10/1976 | Van Scott et al. |
| 4,351,835 A | 9/1982 | Stanko |
| 4,415,576 A | 11/1983 | Stanko |
| 4,548,937 A | 10/1985 | Stanko |
| 4,645,764 A | 2/1987 | Stanko |
| 4,812,479 A | 3/1989 | Stanko |
| 4,874,790 A | 10/1989 | Stanko |
| 4,970,143 A | 11/1990 | Guidoux et al. ............... 435/1 |
| 4,981,687 A | 1/1991 | Fregly et al. |
| 4,988,515 A | 1/1991 | Buckberg ................ 424/529 |
| 5,066,578 A | 11/1991 | Wikman-Coffelt ............ 435/1 |
| 5,075,210 A | * 12/1991 | Wikman-Coffelt ............ 435/1 |
| 5,100,677 A | 3/1992 | Veech ..................... 424/677 |
| 5,134,162 A | 7/1992 | Stanko |
| 5,147,650 A | 9/1992 | Fregly et al. ............... 424/439 |
| 5,210,098 A | 5/1993 | Nath ........................ 514/557 |
| 5,256,697 A | 10/1993 | Miller et al. ............... 514/625 |
| 5,294,641 A | 3/1994 | Stanko ..................... 514/540 |
| 5,312,985 A | 5/1994 | Dhaon et al. ................ 564/143 |
| 5,395,822 A | 3/1995 | Izumi et al. ................. 514/3 |
| 5,472,980 A | 12/1995 | Miller ..................... 514/563 |
| 5,480,909 A | 1/1996 | Stanko ..................... 514/557 |
| 5,508,308 A | 4/1996 | Miller et al. ............... 514/563 |
| 5,536,751 A | 7/1996 | Bunger ..................... 514/557 |
| 5,580,902 A | 12/1996 | Yu et al. |
| 5,612,374 A | 3/1997 | Stanko |
| 5,633,285 A | 5/1997 | Martin ..................... 514/724 |
| 5,648,380 A | 7/1997 | Martin ..................... 514/461 |
| 5,652,274 A | 7/1997 | Martin ..................... 514/724 |
| 5,658,957 A | 8/1997 | Martin ..................... 514/724 |
| 5,667,962 A | 9/1997 | Brunengraber et al. ....... 435/1.2 |
| 5,702,880 A | 12/1997 | Segall et al. |
| 5,714,515 A | 2/1998 | Bunger ..................... 514/557 |
| 5,744,498 A | 4/1998 | Stanko |
| 5,756,469 A | 5/1998 | Beale ....................... 514/23 |
| 5,798,388 A | 8/1998 | Katz ........................ 514/557 |
| 5,801,198 A | 9/1998 | Stanko et al. .............. 514/563 |
| 5,843,024 A | 12/1998 | Brasile ..................... 604/49 |
| 5,863,938 A | 1/1999 | Martin ..................... 514/461 |
| 5,874,479 A | 2/1999 | Martin ..................... 514/724 |
| 5,876,916 A | * 3/1999 | Brunengraber et al. ....... 435/1.2 |
| 5,952,384 A | 9/1999 | Katz |
| 5,968,727 A | 10/1999 | Brunengraber et al. ....... 435/1.2 |
| 6,086,789 A | 7/2000 | Brunengraber et al. ...... 252/399 |
| 6,143,784 A | 11/2000 | Greenhaff et al. |

FOREIGN PATENT DOCUMENTS

| | | |
|---|---|---|
| EP | 0 108 820 B1 | 10/1986 |
| WO | WO 97/41848 | 11/1997 |
| WO | WO 98/04127 | 2/1998 |
| WO | WO 98/51277 | 11/1998 |
| WO | WO 99/21544 | 5/1999 |

OTHER PUBLICATIONS

Banda, M.A. and Granger, D.N., "Mechanism and Protection from Ischemic Intestinal Injury," *Transplantation Proceedings*, 28:2595–2597 (1996).

Cicalese, L., et al., "Pyruvate Prevents Ischemia–Reperfusion Mucosal Injury of Rat Small Intestine," *Amer. J. of Surg.*, 171:97–100; discussion 100–101 (1996).

Crestanello, J.A., et al., "Pyruvate Improves Myocardial Tolerance to Reperfusion Injury by Acting as an Antioxidant: A Chemiluminescence Study," *Surgery*, 124:92–99 (1998).

(List continued on next page.)

*Primary Examiner*—Christopher S. F. Low
*Assistant Examiner*—Donna Jagoe
(74) *Attorney, Agent, or Firm*—Hamilton, Brook, Smith & Reynolds, P.C.

(57) ABSTRACT

A therapeutic composition comprising an alkyl, aralkyl, alkoxyalkyl or carboxyalkyl ester of 2-ketoalkanoic acid and a component for inducing and stabilizing the enol resonance form of the ester at physiological pH values is disclosed. The composition of the invention further comprises a pharmceutically acceptable carier vehicle in which the enol resonance form of the ester is stabilized at physiological pH values. Formulations containing the compositions of the invention permit the successful use of 2-ketoalkanoic acid esters, e.g., pyruvic acid esters, to treat, e.g., ischemic events, shock, organ reanimation, resuscitation and other recognized pyruvate-effective treatments. The compositions of the inventions are also useful in a process for preserving organ parts, organs or limbs removed from a living mammal and in need of preservation, e.g., for later transplantation to an organ recipient.

10 Claims, 4 Drawing Sheets

OTHER PUBLICATIONS

DeBoer, L.W., et al., "Pyruvate Enhances Recovery of Rat Hearts After Ischemia and Reperfusion by Preventing Free Radical Generation," *American Journal of Physiology,* 265:H1571–H1576 (1993).

Kurose, I., et al., "Ischemia/Reperfusion–Induced Microvascular Dysfunction: Role of Oxidants and Lipid Mediators," *Amer. J. Physiol.,* 272:H2976–H2982 (1997).

Margolis, S.A. and Coxon, B., "Identification and Quantitation of the Impurities in Sodium Pyruvate," *Analytical Chemistry,* 58:2504–2510 (1986).

O'Donnell–Tormey, J., et al., "Secretion of Pyruvate. An Antioxidant Defense of Mammalian Cells," *J. of Experimental Medicine,* 165:500–514 (1987).

Perera, A., et al., "High Resolution $^1$H NMR Investigations of the Reactivities of Alpha–Keto Acid Anions with Hydrogen Peroxide," *Free Radical Research,* 26:145–157 (1997).

Salahudeen, A.K., et al., "Hydrogen Peroxide–induced Renal Injury: A Protective Role for Pyruvate In Vitro and In Vivo," *Journal of Clinical Investigation,* 88:1886–1893 (1991).

Sawyer, D.T., et al., "Reactivity of Superoxide Ion with Ethyl Pyruvate, α–Diketones, and Benzil in Dimethylformamide," *Journal of Organic Chemistry,* 48:3733–3736 (1983).

Starostin, E.K., et al., "Decomposition of the Peroxides of the Esters of Keto Acids by Fe(II) Salts," *Bulletin of the Academy of Sciences of the USSR Division of Chemical Science,* 29:109–112 (1980).

Varma, S.D., et al., "Prevention of Intracellular Oxidative Stress to Lens by Pyruvate and Its Ester," *Free Radical Research,* 28:131–135 (1998).

Sims, C.A., et al., "Intravenous Pyruvate and Pyruvate Ethyl Ester Ameliorate Intestinal Mucosal Injury Following Ischemia/Reperfusion," *Surgical Forum,* vol. L: 246–248 (1999).

Bünger, R., et al., "Pyruvate–enhanced Phosphorylation Potential and Inotropism in Normoxic and Postischemic Isolated Working Heart," *European Journal of Biochemistry,* 180(1):221–223 (1989).

Borle, A.B. and Stanko, R.T., "Pyruvate Reduces Anoxic Injury and Free Radical Formation in Perfused Rat Hepatocytes," The American Physiological Society, G535–G540 (1996).

* cited by examiner

R₁ = Methyl, ethyl, propyl, isopropyl, n-butyl, sec-butyl, isobutyl, tertbutyl, pentyl, 4-methylpentyl, 3-methylpentyl, hexyl, heptyl, octyl, 1-phenylmethyl, 2-phenyl-ethyl;

R₂ = Ethyl, propyl, isopropyl, n-butyl, sec-butyl, isobutyl, tertbutyl, pentyl, 4-methylpentyl, ethoxymethyl, 2-ethoxyethyl, carboxymethyl, ethoxycarbonylmethyl.

FIGURE 2

1) Na Pyruvate

2) Na Pyruvate hydrate

3) Ethyl pyruvate

4) Na enolpyruvate

5) Ethyl enolpyruvate

6) Ca enol ethyl ester

7) Parapyruvate

PYRUVATE ESTER COMPOSITION AND METHOD OF USE FOR RESUSCITATION AFTER EVENTS OF ISCHEMIA AND REPERFUSION

CROSS REFERENCE TO RELATED APPLICATIONS

This application is a Continuation of PCT Application Ser. No. PCT/US00/27758, filed Oct. 6, 2000, which claims the benefit of U.S. Provisional Application Ser. No. 60/158,091, filed Oct. 7, 1999, the entire teachings of both of which are incorporated herein by reference.

STATEMENT REGARDING FEDERALLY SPONSORED RESEARCH OR DEVELOPMENT

Part of the work leading to this invention was carried out with United States Government support provided under a grant from the Hational Institutes of Health, Grant No. GM37631. Therefore, the U.S. Government has certain rights in this invention.

BACKGROUND OF THE INVENTION

This invention relates to several new pyruvate compounds and methods for resuscitation and reanimation of mammals, especially humans, before, during and after, e.g., (1) mesenteric ischemia, mesenteric thrombus or mesenteric venous occlusion; (2) aortic aneurism repair, coronary artery bypass, surgical treatment of arterial occlusion of limbs; (3) hemorrhagic shock, resulting from either penetrating and blunt trauma; and (4) preservation and transplantation of organs. Ischemia is defined herein as the interruption of oxygen supply, via the blood, to an organ or to part of an organ. Examples of ischemic events include (i) myocardial, cerebral, or intestinal infarction following obstruction of a branch of a coronary, cerebral, or mesenteric artery, and (ii) removal and storage of an organ prior to transplantation. In the case of myocardial infarction, prompt restoration of blood flow to the ischemic myocardium, i.e. coronary reperfusion, is a key component of the treatment. This is because mortality is directly related to infarct size (tissue necrosed) which is related to the severity and duration of the ischemic event. The consequences of hemorrhagic shock are similar to those of ischemia, although the causative event is not an interruption of blood flow but rather the event of massive blood loss itself which causes deprivation of the oxygen supply.

Notwithstanding the need to supply an organ cut-off from a normal blood supply with oxygen, it has been found that reperfusion injury may occur upon restoration of blood flow. This results from the production of reactive oxygen species (ROS), namely, hydrogen peroxide, hydroxyl radicals and superoxide radicals, among others, which are formed from both extracellular and intracellular sources. ROS are highly reactive species that, under normal conditions, are scavenged by endogenous defense mechanisms. However, under conditions of post-ischemic oxidative stress, ROS interact with a variety of cellular components, causing peroxidation of lipids, denaturation of proteins, and interstitial matrix damage and resulting in increase of membrane permeability and release of tissue enzymes.

In an attempt to minimize these undesirable side effects of perfusion in the treatment of ischemia and also of shock, researchers have demonstrated the utility of various antioxidants in the reperfusion process.

Banda et al. (1996), together with Kurose et al. (1997), suggested the use of an inhibitor of ROS production to protect the reperfused myocardium and the use of agents and inhibitors that reduce ROS levels. In a similar context, desiring to provide more efficient resuscitation, researchers have demonstrated the additive utility of incorporating an antioxidant and a beneficial metabolic fuel into the reperfusion regimen. Salahudeen et al. (1991) used solutions of pyruvate, an ROS scavenger and a metabolically important precursor fuel for gluconeogenesis, to protect against hydrogen peroxide induced acute renal failure. Cicalese et al. (1996) found that pretreatment with intraluminal pyruvate ameliorates post ischemic small bowel injury while Crestanello et al. (1998), DeBoer et al. (1993), and O'Donnell-Tormey et al. (1987) have substantiated this finding by examining the ameliorative effects of both endogenously secreted pyruvate and exogenously added material in the reperfusion and subsequent function of organ and tissue preparations subjected to ischemia and simulated shock. Varma et al. (1998), similarly, have shown that in a cultured lens system, after exposure of the cultured lens to free radical oxidant stress, pyruvate and its esters have certain cytoprotecting and restorative effects.

In a further effort directed to protecting reperfused heart tissue, U.S. Pat. No. 5,075,210, herein incorporated by reference, discloses a process for reperfusing a heart for transplantation. The patent discloses a cardioplegic solution containing sodium chloride, potassium chloride, calcium chloride, sodium bicarbonate, sodium EDTA, magnesium chloride, sodium pyruvate and a protein.

U.S. Pat. No. 5,294,641, herein incorporated by reference, is directed to the use of pyruvate to prevent the adverse effects of ischemia. The pyruvate is administered prior to a surgical procedure to increase a patient's cardiac output and heart stroke volume. The pyruvate is administered as a calcium or sodium salt. The pyruvate can alternatively be an amide of pyruvic acid such as ethylamino pyruvate. Similarly, U.S. Pat. No. 5,508,308, herein incorporated by reference, discloses the use of pyruvyl glycine to treat reperfusion injury following myocardial infarction.

U.S. Pat. No. 4,988,515 and 5,705,210, herein incorporated by reference, use pyruvate salts in cardioplegic solutions and in preservation solutions for the heart before transplantation. U.S. Pat. No. 4,970,143, herein incorporated by reference, discloses the use of acetoacetate for preserving tissue, including addition of the pyruvate to the preservation solution.

U.S. Pat. No. 5,100,677 herein incorporated by reference, discloses the composition of various parenteral solutions. Of interest is a recommendation to include pyruvate anions (apparently from metal salts) in intravenous solutions.

U.S. Pat. No. 5,798,388, herein incorporated by reference, further describes the utility of pyruvate salts and of various complex derivatives, such as amides, for the treatment of ROS in the context of airway inflammation. The patent discloses a pyruvate compound in the form of a covalently linked pyruvoyl-amino acid. By utilizing this type of a pyruvate delivery system, the negative effect of pyruvate salt is avoided. However, administration of large amounts of pyruvate-amino acid may result in nitrogen overload which could harm patients with liver and/or kidney pathology.

In a similar context and based on a similar rationale for pyruvate delivery, U.S. Pat. No. 5,876,916 pertains to the utility of pyruvate thiolesters and polyol esters for the treatment or prevention of reperfusion injury following ischemia, diabetic effects, cholesterol levels, injured organs, ethanol intoxication or as a foodstuff; and U.S. Pat. Nos. 5,633,285; 5,648,380; 5,652,274; and 5,658,957, each herein incorporated by reference, disclose various compositions, salts, prodrugs and derivatives of pyruvate in mixtures with other antioxidants, fatty acids as anti-inflammatory and immunostimulating wound healing compositions. However, administration of large amounts of complex pyruvate-amino acid and other pro-drug derivatives requiring enzymatic hydrolysis prior to liberation of their antioxidant effects may result in nitrogen and/or other xenobiotic overload, which could harm patients directly, interfere with normal detoxifying processes, or cause toxic effects through by-products of limited shelf-life.

Notwithstanding the acceptance of pyruvate as an effective component of a reperfusion solution or other varied applications, pyruvic acid is a strong and unstable acid which cannot be infused as such. On standing in solution, pyruvic acid and its salts at various pH values, including in the physiological range, are known to form both a stable hydrate and a dimer (para-pyruvate), neither of which react with ROS as antioxidants and both of which are known inhibitors of pyruvate utilization as a metabolic fuel, thereby abrogating any of the beneficial effects which might have accrued from pyruvate administration in accordance with the prior art just described.

Furthermore, it has been recognized that traditional pharmacological pyruvate compounds, such as salts of pyruvic acid, are not particularly physiologically suitable. For example, these compounds lead to the accumulation of large concentrations of ions (e.g., calcium or sodium) in the patient's body fluids. Similarly, amino acid compounds containing pyruvate can lead to excessive nitrogen loads. It has also been proposed to infuse pyruvylglycine, the amide function of which is presumably hydrolyzed in plasma and/or tissues, thus liberating pyruvate.

However, at the high rates of pyruvoylglycine infusion required to achieve 1 mM pyruvate in plasma, the glycine load may be harmful to patients suffering from hepatic or renal pathologies. Also, flooding plasma with glycine may interfere with the transport of some amino acids across the blood-brain barrier. Accordingly, while potentially suitable to organ preservation, these pyruvate compounds are less suited to treating an organ in vivo, and it is recognized that a need exists to provide a pyruvate delivery compound that is more physiologically acceptable.

There is also a recognized need to provide a pyruvate delivery system that is cost effective, simple, and devoid of opportunities for contamination because of 1) limited shelf-life, 2) complexity of formulation, 3) reactivity and co-reactivity with excipients and other formulation materials, 4) adverse biochemical reactivity during transport, translocation, and uptake into tissues, and 5) the requirement for metabolic activation via enzymatic hydrolysis by amidases or peptidases. Therefore, it would be desirable to have available an alternate physiologically compatible therapeutic pyruvate compound.

SUMMARY OF THE INVENTION

The invention described herein provides a new and improved, accessible composition for the above-indicated uses.

In one aspect, the invention is directed to a composition comprising an alkyl, aralkyl, alkoxyalkyl or carboxyalkyl ester of 2-ketoalkanoic acid and a component for inducing and stabilizing the enol resonance form of the ester at physiological pH values. The composition of the invention further comprises a pharmceutically acceptable carier vehicle in which the enol resonance form of the ester is stabilized at physiological pH values.

Preferably, the ester in the composition of the invention is an alkyl ester of 2-ketopropionic acid (pyruvic acid), most preferably the ethyl ester, and the stabilizing component is a cationic material, preferably a divalent cation, and most preferably calcium or magnesium. The pharmaceutically acceptable carrier in the composition of the invention can be any carrier vehicle generally recognized as safe for administering a therapeutic agent to a mammal, e.g., a buffer solution for infusion, a tablet for oral administration or in gel, micelle or liposome form for on-site delivery. A preferred buffer solution is isotonic or hypertonic saline; or a bicarbonate, phosphate, plasma extender, microcolloid or microcrystalline solution. Particularly preferred is a Ringer's solution of isotonic saline supplemented with potassium ion. In a particularly preferred aspect, the composition of the invention comprises ethyl pyruvate admixed with calcium ion in a Ringer's solution at a pH in the range of 7–8.

In other aspects, the ester portion of the 2-ketoalkanoic acid ester compound in the composition of the invention is selected preferably from the group consisting of ethyl, propyl, butyl, carboxymethyl, acetoxymethyl, carbethoxymethyl and ethoxymethyl esters. The 2-ketoalkanoic acid portion is selected preferably from the group consisting of 2-keto-butyrate, 2-ketopentanoate, 2-keto-3-methyl-butyrate, 2-keto-4-methyl-pentanoate and 2-keto-hexanoate.

In another aspect, the invention is directed to methods for treating injuries, conditions or disorders associated with events such as ischemic events or reperfusion. Formulations containing the novel compositions of the invention permit the successful use of 2-ketoalkanoic acid esters, e.g., pyruvic acid esters, to treat, e.g., ischemic events, shock, organ reanimation, resuscitation and other recognized pyruvate-effective treatments as sufficiently high loads of pyruvate can be administered without a toxic constituent. Moreover, use of the compositions of the invention provides a direct replacement for traditional lactated Ringer's solutions uncomplicated by the addition of co-active ingredients or complex excipients, such as those comprised of multiple compounds or molecular derivatives of pyruvate itself. The compositions of the inventions are also useful in a process for preserving organ parts, organs or limbs removed from a living mammal and in need of preservation, e.g., for later transplantation to an organ recipient. Such processes are well known to those of skill in the art, e.g., as described in U.S. Pat. No. 5,066,578, hereby incorporated by reference herein.

A further practical advantage of the methods of the invention is the formulation of the active 2-ketoalkanoic acid ingredient as a biologically safe, readily hydrolyzable ester which can be taken up into tissues and cells by diffussive processes through membranes, owing to said ester's greater lipophilicity over the corresponding salt, while retaining the ability to be hydrolyzed intracellularly by means of non-specific esterases and/or non-specific, marginally alkaline solvolysis catalyzed by organic acids or bases such as amino acid residues at physiological pH values.

More importantly, the method of this invention provides 2-ketoalkanoic acids, e.g., pyruvic acid, in a stabilized ester form that inactivates reactive oxygen species by more than one mechanism of reaction and whose reaction products with reactive, hypervalent oxygen, such as hydrogen peroxide, affords degradation products that themselves are metabolic fuels instead of potentially harmful excretory products or metabolites.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Accordingly, it is a primary object of this invention to provide new and improved compositions containing 2-ketoalkanoic acid esters and methods of using them to treat certain conditions as described above.

Figure 1:
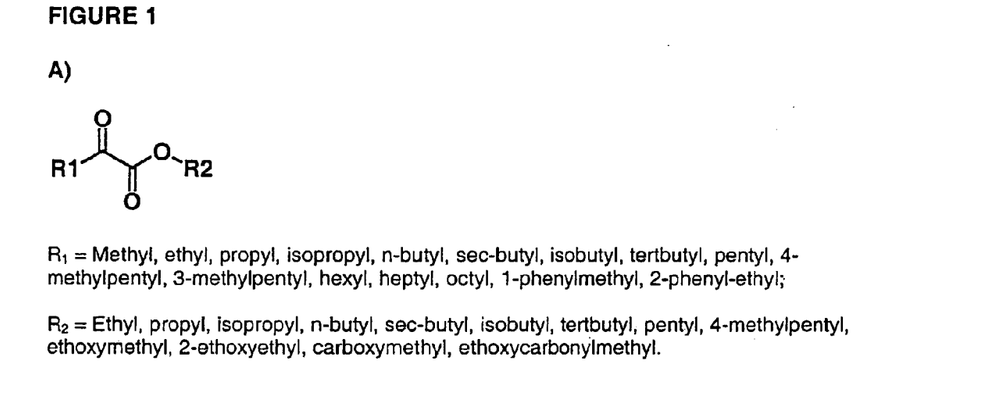
FIG. 1 shows the structures of the preferred 2-ketoalkanoic acid esters in the composition of the invention.

To achieve the foregoing objects and in accordance with the purpose of the invention, as embodied and broadly described herein, one novel composition of this invention comprises a 2-ketoalkanoic acid ester, in accordance with the molecular structures shown in FIG. 1, admixed with a sufficient concentration of biologically safe organic or inorganic cations to induce enolization of the 2-keto functionality of the ester at physiological pH values. In a preferred embodiment, the composition comprises an alkyl ester of 2-ketopropionic acid (pyruvic acid), the ester is the ethyl analog and the cation is a divalent cation, particularly either calcium or magnesium. In a particularly preferred formulation of the composition of the invention, the ester compound is ethyl pyruvate admixed with calcium ion in a Ringer's solution at a pH of about 7–8.

The therapeutic compositions of the invention may be administered orally, topically, or parenterally, (e.g., intranasally, subcutaneously, intramuscularly, intravenously, intraluminally, intra-arterially, intravaginally, transurethrally or rectally) by routine methods in pharmaceutically acceptable inert carrier substances. For example, the therapeutic compositions of the invention may be administered in a sustained release formulation using a biodegradable biocompatible polymer, or by on-site delivery using micelles, gels, liposomes, or a buffer solution. The active ester agent in the composition of the invention can be administered, as an infusate, at a concentration of, e.g., 20–200 mM, at a rate of, preferably, 10–100 mg/kg/hr, in a buffer solution as described herein. In bolus form, the active ester agent can be administered at a dosage of, e.g., 10–200 mg/kg from 1–4 times daily. The cation in the composition of the invention is at an appropriate concentration to induce enolization of the 2-keto functionality of the amount of active ester agent in the administered composition. Optimal dosage and modes of administration can readily be determined by conventional protocols.

It is believed that pyruvate, and other 2-ketoalkanoic acids, when liberated intracellularly from the esters delivered, e.g., by the reanimation perfusate, acts as a NADH trap and a trap for ROS generated upon reperfusion. In the first instance, a 2-ketoalkanoic acid reacts to afford lactate, oxidizing excess NADH and thereby protecting against the "reductant stress" generated during the physiological insult caused by hypoxia. In the latter instance, a 2-ketoalkanoic acid reacts with hypervalent oxygen, as demostrated in the prior art, to form a transient peracid which decomposes spontaneously, and eventually, to acetate and carbon dioxide. The resulting acetate is a waste product, which may be salvaged by re-entry into the acetylCoA pool and harvested biochemically via intermediary metabolism in the Krebs cycle or via gluconeogenesis.

However, and more significantly for the purposes of this invention, the 2-ketoalkanoic acid ester itself serves as an antioxidant by a different mechanism, namely, via reaction with hypervalent oxygen at the enol methylene group. ROS is a membrane associated process, since hypervalent oxygen is generated by a redox cascade mediated by cytochromes in the microsomes or the mitochodria. It is also an intracellular process that takes place in a lipophilic environment rather than in cytosol, and the thermodynamic properties of a 2-ketoalkanoic acid ester are such that its reactivity towards redox reaction in a lipophilic phase is putatively favored by the cation mediated keto-enol equilibrium. Ab initio and semi-empirical thermodynamic analyses on ethyl pyruvate as a representative enolizable molecule in the presence of calcium are discussed in greater detail as part of Example I below.

For example, using pyruvate as the exemplary 2-ketoalkanoic acid, formation of transient epoxides and subsequent rearrangement affords the corresponding hydroxylated pyruvate esters at the 3-carbon, by a mechanism similar to that of 3-hydroxy-pyruvate formation in intermediary metabolism as well as that of carbon additions to the phosphoenolpyruvate congener. Hydroxylation alpha to keto groups is also a recognized cytochrome mediated process in steroid metabolism and in microsomal hydroxylation of drugs. The resulting hydroxy-pyruvates, in turn, when solvolyzed into the carboxylic anions, can then react once again with hypervalent oxygen to afford hydroxyacetic acid (glycolic acid), the net result being that pyruvate esters can ultimately quench two equivalents of ROS while pyruvates are limited thermodynamically to quenching only one. As mentioned above, 2-ketoalkanoic acid esters other than pyruvate esters are also appropriate for use in compositions of the invention as long as the active compound is metabolizable as described above for the pyruvate ester.

The following examples are presented to illustrate the advantages of the present invention and to assist one of ordinary skill in making and using the same. These examples are not intended in any way otherwise to limit the scope of the disclosure.

EXAMPLE 1

Thermodynamic Modeling Of Pyruvate Esters

Semiempirical quantum chemistry permits the comparative evaluation of various pyruvate analogs with regard to the properties that determine each molecule's reactivity. As one can note a marked difference in the biological effect of ethyl pyruvate versus sodium pyruvate as antioxidants, the hypothesis that these two molecules are thermodynamically different can be tested by Huckel Molecular Orbital (HMO) analysis followed by Complete Neglect of Differential Overlap Analysis (CNDO), using Molecular Modeling Pro/ MOPAC software (ChemSW, Inc. Fairfield, CA). The following results were obtained for the structures shown in FIG. 2, after their conformations were set by energy minimization to the optimal conformation:

TABLE 1

Comparison of Thermodynamic Properties

| Compound | Energy | Dipole | LogP | H-Acceptor | H-Donor |
|---|---|---|---|---|---|
| Na Pyruvate (1) | −31.7 | 355.6 | −85.9 | 17.8 | 2.9 |
| Na Pyruvate hydrate (2) | −16.5 | 462.8 | −71.2 | 23.9 | 4.8 |
| Na Enol-pyruvate (3) | −30.7 | 358.0 | −72.1 | 17.7 | 2.8 |
| Ethyl pyruvate (4) | −86.5 | 2.8 | −.21 | .73 | 8.5 |
| Ethyl enol-pyruvate (5) | −84.1 | 2.5 | −.37 | .71 | 7.3 |
| Ca enol ethyl pyruvate (6) | −82.3 | 2.7 | −.41 | .85 | 7.2 |

From the trend in minimization energies, the lower and, therefore, the more stable configurations are those associated with the pyruvate esters, although the differences all fall within an order magnitude. On the other hand, the esters show markedly lower dipole moments, reflecting their relatively weak ionization and dissociation potentials, a fact that is further supported by the higher LogP values, which are a measure of relative lipophilicity. Also, the esters are poorer hydrogen bonding acceptors and better hydrogen bonding donors, consistent with their dipolar and lipophilic properties.

Thus, on an ab initio thermodynamic basis, one would predict that ethyl pyruvate, and its putative enol tautomers, are more likely to partition between a polar aqueous phase and a lipid phase, while retaining conformational stability of the same order as the pyruvate sodium salts. Further, it should be noted that the coordination complex of the pyruvate enolate ester with a divalent cation, such as calcium, shown in FIG. 2 as structure 6, affords the most pronounced change in properties over pyruvate itself, substantiating the utility of these cation-enolate-ester complexes as promoters of heretofore unexploited reactivities of the pyruvate carbon skeleton conformation.

EXAMPLE 2

Reactivity Modeling Of Pyruvate Esters

Figure 2:
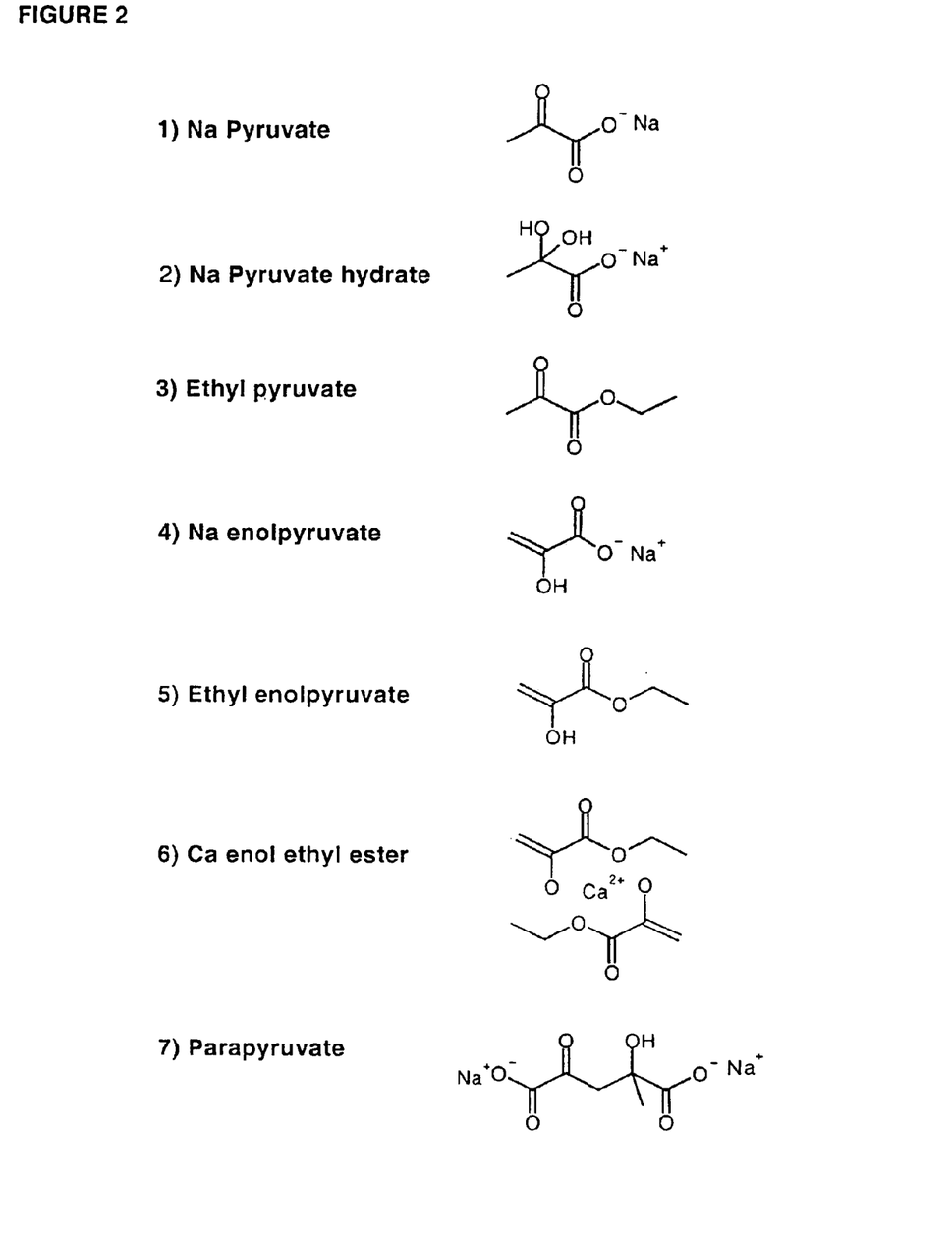
FIG. 2 shows the structures of certain preferred esters in the composition of the invention, their enol resonance structures and the structures of certain prior art compounds.

Searches of the Chemical Abstracts and the ISIS databases (MDL Information Systems, Inc.) were conducted to uncover actual examples of the reactivity of pyruvates and their enolates. While numerous precedents for the reactions of pyruvate salts have been recorded, far fewer examples of the molecular interactions between pyruvate esters and hypervalent oxygen are reported in the organic and biochemical literature. The principal reactions of pyruvates at physiological pH values are hydrate formation (FIG. 2, structure 2) and dimerization to para-pyruvate (FIG. 2, structure 7).

As reported by Margolis et al. (1986), sodium pyruvate at concentrations of 1 Mol/liter or less forms varying amounts of the hydrate and the linear dimer, 4-hydroxy-4-methyl-2-ketoglutaric acid. The hydrate can reach 6–10% and the dimer 20–25% on standing for 48 hrs. This reactivity pattern is an important consideration in the evaluation of sodium pyruvate-containing infusates and perfusates, since the hydrate is unreactive towards hypervalent oxygen and the dimer is an inhibitor of 2-ketoglutarate dehydrogenase, a mitochondrial respiratory enzyme, as well as an inhibitor of glutamate transaminases and lactic acid dehydrogenase. By contrast, neither hydrate formation nor dimerization of pyruvate esters have been reported in the chemical literature.

While the enol forms of pyruvate are thermodynamically stable in principle, their occurrence in aqueous media is unfavored and half-lives of enolates are measurable only in the 3–5 sec range (Kuo et al. (1979)). As the polarity of the solvent decreases, exemplified by the solvation environment provided by dimethylsulfoxide or dimethylformamide, the half life of the enol increases by at least two orders of magnitude (Chiang et al. (1993); Peliska et al. (1991); Sawyer et al. (1983).

As to reactivity toward hypervalent oxygen, both pyruvate salts and pyruvate esters react to form an initial hydroperoxide intermediate at the carbonyl site, which rearranges by disproportionation to afford acetic acid and carbon dioxide or ethoxycarbonic acid, which undergoes subsequent aqueous solvolysis into carbon dioxide and ethanol (Constantopoulos et al (1984); Sawyer et al. (1983); Starostin et al. (1980)).

However, enolpyruvates can also react by an alternate mechanism that involves addition to the exo-methylene group, as in the case of enolpyruvate C-bromination at the 3-carbon (Sekine et al. (1980)), the chelation controlled addition to allylic compounds (Muderawan et al. (1998)), and the biological addition of carbon dioxide to form oxaloacetate via phosphoenolpyruvate carboxylase (Ausenhus et al. (1992)). Enols of biological ketones in general, as exemplified by D-ring acetyl steroids, react with activated oxygen via the cytochrome P-450 oxidase system to afford hydroxyketones via a transient exomethylene epoxide intermediate (Yamazaki et al. (1997)).

When evaluated on the grounds of thermodynamic likelihood and chemical precedent, pyruvate salts can be predicted, via the REACCS software database correlation system, to react with hypervalent oxygen to afford only decarboxylation to acetate and carbon dioxide. Pyruvate esters, on the other hand, can be expected to afford not only the paired decarboxylation products, acetate and alcohol, but also hydroxylated adducts at the 3-carbon, most probably a 3-hydroxypyruvate. These latter species can again react with hypervalent oxygen to yield glycolic acid and carbon dioxide (Perera et al. (1997)), thereby consuming two equivalents of oxidant.

EXAMPLE 3

Stability And Reactivity Of Pyruvate Esters In Solution

Based on the foregoing modeling exercises, the following hypothesis driven experiments provide verification in chemical and biological systems and further differentiate the method of this invention from prior art.

Ethyl pyruvate affords a more stable aqueous solution than sodium pyruvate in the presence of calcium salts (Ringer's solution), and this observation can be extended to the study of other pyruvate analogs, as shown in FIG. 1, by dissolving them in Ringer's solution containing at least 0.2 equivalent of calcium per molar equivalent of pyruvate analog titrated with sodium hydroxide, or other suitable inorganic alkali, to physiological pH values. Specifically, the preferred embodiment of this "pyruvated" Ringer's solution for use in NMR, stability, and subsequent biological studies is shown in Table 2. It is to be understood that the pyruvate analog in the instant example may be substituted with any of the analogs shown in FIG. 1 at any concentration sufficient to afford a homogenous solution or substituted by control substances for comparative purposes, such as pyruvic acid, lactic acid (as would be the case in "lactated" Ringer's solution and other reference or inactive ketoacid analogs. The calcium cation may also be substituted, e.g., with magnesium or any other biologically safe cation capable of substituting for calcium and stabilizing the formation of transient coordination complexes with pyruvate ester enolates in aqueous solution.

TABLE 2

Constituents of Pyruvated Ringer's Solution

| Component | Composition | Range |
|---|---|---|
| Isotonic saline | 75 cc | — (fixed) |
| KCl | 11.25 | — (fixed) |
| $CaCl_2$ | 7.5 mg | 5–20 mg |
| Ethyl pyruvate | 0.781 ml | 0.5–1.5 ml |
| NaOH | To pH 7.5 | 7.35–7.55 (pH) |

Following the procedural recommendations for analysis of Margolis et al. (1986) with respect to scanning times and frequencies on a 400 MHz spectrometer operating in pulse. Fourier transform mode, both proton and carbon shifts in the characteristic resonances for each carbon and proton cluster at the enolizable carbon were monitored as a function of time and demonstrated that a greater proportion of pyruvate esters showed a propensity to enolize in Ringer's solutions, especially those containing calcium or magnesium, while pyruvate acid anions showed preponderant hydration and dimerization under similar conditions. The ultraviolet absorptions of these solutions were also measured periodically over the 230–260 nm range and 300–340 nm span, where changes in enol formation become evident, and provided confirmatory evidence about the distinctly different salvation properties of pyruvate ester analogs in comparison to pyruvate salts applied in the various methods of prior art.

The experimental sequence in which to establish the greater utility of the pyruvate derivatives in this invention follows along the same lines as the comparative spectral experiments just described. The same solutions of test substances used to demonstrate enolization and related phenomena were also used in the comparison of basal values for each candidate pyruvate to the effects of oxidants on the disappearance of characteristic pyruvate resonances and the appearance of acetate or other degradants of the initial test preparation as a function of exposure to these oxidants.

For example, 1 mMolar solutions of pyruvic acid and ethyl pyruvate showed average absorption values, corrected for blanks, of 0.15 and 0.2 respectively at 230–260 nm in the absense of calcium at pH 7.2; addition of calcium had no effect on pyruvate, which showed only a marginal increase in absorption to 0.16, while ethyl pyruvate rose twofold to 0.41 in 3 replicate experiments with a coefficient of variation of less than 15%. When 28 mM solutions were examined in a similar manner at 300–340 nm, the absorbance of pyruvate remained unchanged before and after calcium addition at a value of 0.03, while the ethyl pyruvate solutions become noticeably straw colored to the naked eye, rising in absorbance from 0.07 to 0.85. The yellow coloration and increases in spectrophotometric absorption in the ultraviolet region confirms the formation of a 1,3-conjugated ketone system, as would result from the enolization of ethylpyruvate under conditions which appear not to enolize pyruvic acid.

Thus, applications of hypervalent oxygen mimics, whose redox potential is known to be a model for ROS, such as hydrogen peroxide, Fenton's reagent, and meta- chloroperbenzoic acid, were dispensed into the test solutions at concentrations ranging from 1 to 50 mMolar and their degradative effects noted. It was shown that pyruvate esters consume a greater proportion of oxidant per molar equivalent than their congeneric free acid analogs.

EXAMPLE 4

Stability and Reactivity of Pyruvate Esters In Tissue Culture

Pyruvate esters, and in particular ethyl pyruvate, in the presence of calcium ion are sufficiently lipophilic to be taken up by cells at a faster rate than equimolar amounts of pyruvate in the cell preparation perfusate. Moreover, the compounds of this invention serve as prodrugs for intracellular pyruvate delivery and are, therefore, utilized as antioxidants in part by direct decarboxylation of the pyruvate moiety that is delivered intracellularly and made bioavailable after non-specific ester solvolysis by ubiquitous cytosolic carboxylesterases. Prior to hydrolysis intracellularly, these pyruvate esters also react beneficially via enol-mediated, transient epoxidation mediated by hypervalent oxygen, and related toxic oxidants, to form 3-hydropyruvates.

The resulting hydroxypyruvate esters, especially in the case of ethyl pyruvate and its analogs which are depicted in FIG. 1, are then taken up as a metabolic fuel by anapleurotic incorporation, after solvolysis, or subjected to further decarboxylative oxidation by additional equivalents of reactive oxygen species to form the corresponding hydroxyacetates (glyoxylic acids). Thus, it is to be understood that pyruvate esters can quench twice as many reactive oxygen species than the non-enolyzing forms of the corresponding unesterified ketoacid anion; that is, first by the formation of 3-hydroxypyruvates and then by the latter's decarboxylative degradation into a smaller metabolite, which like acetate can be readily incorporated into intermediary metabolism. These outcomes in which the compounds of this invention prove more effective antioxidants, as well as metabolic fuels, after exposure to ROS are demonstrable by combinations of NMR and spectral (UV) analytical procedures that follow, for example, the fate of stable isotope labeled pyruvate[3—$^{13}$C] species under various experimental conditions.

Accordingly, cell and tissue cultures present a effective means for comparing the relative rates of uptake and subsequent disposition of pyruvate analogs dispensed into the culture or perfusion medium and then monitored for incorporation into cells by means of a stable isotopic tracer that is amenable to proton and carbon magnetic resonance analysis in real time or by mean of mass spectral analysis of suitable extracts of the test biomass after a suitable period of incubation or perfusion.

In particular, since bowel ischemia is one of the more damaging conditions for which pyruvates are known to provide rescue and resuscitation, the use of enterocyte cell cultures provides a appropriate test model. This model consists of exposing enterocytes after a basal period under various conditions of anoxia and then hyperoxia to a perfusate containing Ringer's solution supplemented with calcium as control and then various tests compositions of pyruvates, including sodium pyruvate, all labeled at the 3-methyl position with $^{13}$C. For the carbon MR experiments, cells are seeded on the surface of polystyrene microcarrier beads in bacteriological Petri dishes and grown for 3 days to confluency before harvesting and spectroscopic analysis, following the method of Artemov et al. (1998) and modeling rubrics of Yu et al. (1997) and of Vogt et al. (1997). The test perfusates during the study period are also monitored for purposes of background subtraction from the acquisition of carbon resonances characteristic of the Krebs cycle.

Thus, the rate of carbon flux of exogenously added pyruvate can be followed throughout the process of conversion into citrate and ketoglutarate/glutamic acid. The 3-carbon of pyruvate and the 2-carbon of acetate, derived from pyruvate, are expected to provide differential enrichments at the 2 versus the 4 position of citrate and ketoglutarate. Direct incorporation of the pyruvate carbon skeleton into citrate and ketoglutarate should be expressed as a faster increase in label at the 2 position versus the 4 position, since the latter is more likely to be diluted by the larger acetate-acetyl-CoA pool.

If hydroxypyruvate is formed in the reaction, not only can the methyl group resonance be detected directly, but the subsequent utilization of hydroxypyruvate via decarboxylation into glyoxylate and homologation to malate can also be traced by the same scheme of differential labeling analysis. Experiments of this nature confirm that pyruvate esters act differently as a carbon source from pyruvate salts. Furthermore, such experiments confirm that lactate, acetoacetate and related esters, when substituted for pyruvate esters, do not show enolization and are not incorporated into cells and/or processed via oxidative metabolism in a manner similar to, and to the extent of, the pyruvate esters used in the method of this invention.

EXAMPLE 5

Application Of The Invention In Ischemia Rescue

Figure 3:
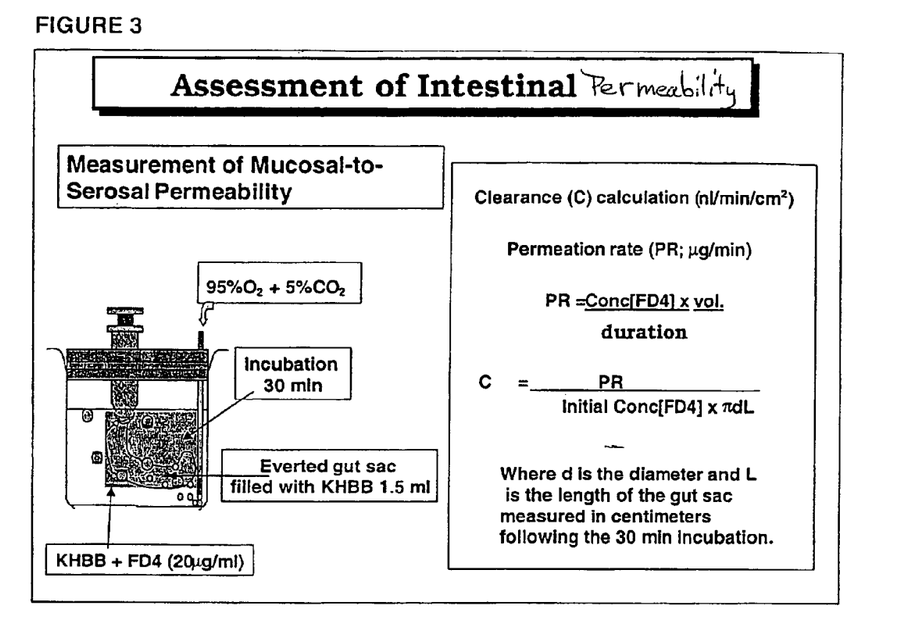
FIG. 3 shows the system and computational parameters used for the measurement of mucosal-to-serosal intestinal permeability following practice of the method of the invention.

The utility of ethyl pyruvate in a Ringer's solution infusate as a resuscitation fluid in ischemia/reperfusion mucosal injury and barrier dysfunction is demonstrated in this illustrative experiment using a rat model of superior mesenteric artery occlusion. The model system and calculation parameters are illustrated in FIG. 3.

After induction of general anesthesia using intraperitoneal ketamine and pentobarbital, male Sprague-Dawley rats (250–350 g) were subjected to 60 minutes of superior mesenteric artery occlusion followed by 60 minutes of reperfusion. Heart rate and mean arterial blood pressure were measured via a right carotid arterial catheter. The left internal jugular vein was cannulated for intravenous infusions.

Controls (n=6) received lactated Ringer's solution (lactate, 28 nM, 111.5 ml/kg/hr infusion, 1.5 ml/kg bolus prior to ischemia, and a 3.0 ml/kg bolus prior to reperfusion). Experimental groups (n=6 each) received similar volumes (3 ml) of either pyruvate, Na salt (28 mM) or pyruvate ethyl ester (28 mM), prepared in accordance with the method of this invention as shown in Table 2 and at a dosage rate equivalent to 10 mg/kg/hr. Small intestinal mucosal-to-serosal permeability ($C_{MS}$, nl/min/cm$^2$) of FITC- dextran (mw=4 kDA) was evaluated using an everted gut sac technique as previously described by Wattanasirichaigoon (1999). Permeability was measured at baseline, after 30 and 60 minutes of ischemia (I30 and I60) respectively, and after 30 and 60 minutes of reperfusion (R30 and R60, respectively). Histologic samples at baseline, I60 and R60 were evaluated for villous height (VH, $\mu$) and mucosal thickness (MT, $\mu$). Mucosal injury grade was determined according to the method described by Chiu et al. (1970), scored as in Table 3, as follows:

TABLE 3

Mucosal Injury Grade

| | |
|---|---|
| Grade 0 | Normal Mucosa |
| Grade 1 | Subepithelial space formation |
| Grade 2 | Moderate epithelial lifting confined to the tip of the villi |
| Grade 3 | Extensive epithelial lifting, a few tips are denuded |
| Grade 4 | Denuded villi, dilated exposed capillaries, increased cellularity in the lamina propria |
| Grade 5 | Hemorrhagic ulceration |

Data were summarized as means±standard error of the mean. Significances of differences were determined using Student's t-test. Differences were considered significant for $p<0.05$.

Figure 4:
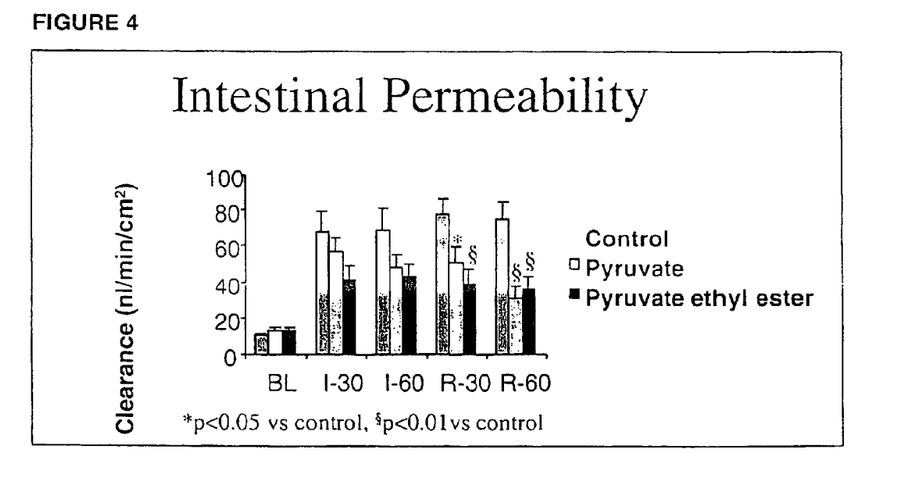
FIG. 4 shows the intestinal permeability results achieved for a control composition relative to compositions of the invention.
Figure 5:
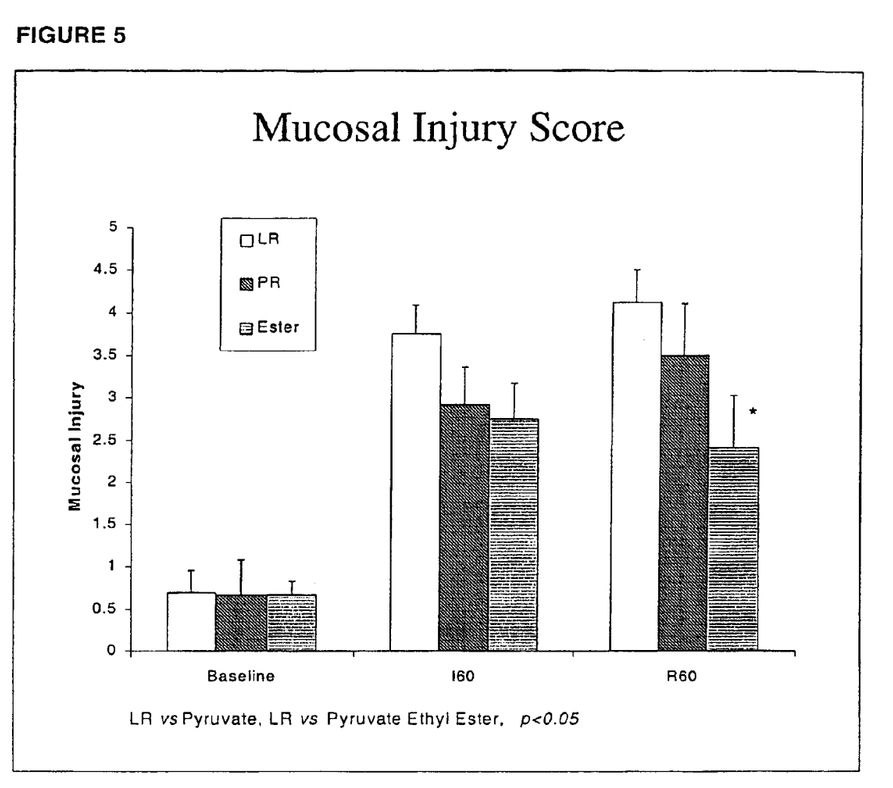
FIG. 5 shows the results obtained for mucosal injury scores for compositions of the invention.

The results of these experiments on the utility of the method of invention revealed that both pyruvate compositions, as free acid as well as ethyl ester, significantly decreased mucosal permeability during reperfusion, as shown in FIG. 4. The ester showed a significant trend towards effecting earlier and greater cytoprotection as judged by the extent of permeability increase, which is a sign of irreversible tissue damage and in terms of the significant diminution in mucosal injury score, shown graphically in FIG. 5. Pyruvate ethyl ester, moreover, significantly maintained villous height and mucosal thickness during both ischemia and reperfusion ($p<0.01$) as shown in Table 4:

TABLE 4

Histological Findings on Beneficial Effects of "Pyruvated" Ringer's Solution

| | Lactate | | Pyruvate | | Pyruvate Ester | |
|---|---|---|---|---|---|---|
| | VH | MT | VH | MT | VH | MT |
| Baseline | 470 ± 30 | 553 ± 34 | 461 ± 25 | 524 ± 28 | 486 ± 12 | 583 ± 8 |
| I60 | 244 ± 20 | 298 ± 32 | 290 ± 30 | 372 ± 36 | 381 ± 24§ | 466 ± 25§ |
| R60 | 130 ± 25 | 141 ± 22 | 201 ± 44 | 266 ± 50 | 296 ± 26§ | 352 ± 34§ |

Note: Lactate vs Pyruvate and Lactate vs Pyruvate Ester, p < 0.05 and §p < 0.01

Taken as a whole, these findings confirm the utility of pyruvate esters in the method of this invention in compositions for the treatment of ischemia and related conditions caused by hypoxia and then reperfusion, with its attendant reactive oxygen damage. The model system described above, a rat model of superior mesenteric artery occlusion, is a standard model system familiar to those of ordinary skill who wish to provide therapeutic treatment of the kind described, and the results reported above are easily extrapolatable for human use.

Thus, it is apparent that there has been provided, in accordance with the invention, novel 2-ketoalkanoic acid ester compounds and compositions and methods of treating the deleterious effects of hypervalent oxidants resulting from hypoxic damage, followed by reperfusion, that fully satisfies the objects, aims and advantages set forth above.

REFERENCES

Artemov, D., Bhujwalla, Z. M., Pilatus, U. and Glickson, J. D., Two compartment model for determination of glycolytic rates of solid tumors by in vivo 13C NMR spectroscopy. NMR in Biomedicine 11:395–404, 1998.

Ausenhus, S. L. and O'Leary, M. H., Hydrolysis of phosphoenolpyruvate by phosphoenolpyruvate carboxylase from Zea mays. Biochemistry 31:6427–6431, 1992.

Banda, M. A., and Granger, D. N., Mechanism and protection from ischemic intestinal injury. Transplantation Proceedings 28:2595–2597, 1996.

Chiang, Y., Kresge, A. J. and Pruszynski, Keto-enol equilibria in the pyruvic acid system: determination of the keto-enol equilibrium constants of pyruvic acid and pyruvate anion and the acidity constant of pyruvate enol in aqueous solution. Journal of the American Society 114:303–310, 1992.

Chiu, C. J., McArdle, A. H., Brown, R., Scott, H. J. and Gurd, F. N., Intestinal mucosal lesion in low-flow states.I. A morphological, hemodynamic, and metabolic reappraisal. Archives of Surgery 101:478–483, (1970).

Cicalese, L., Lee, K., Schraut, W., Watkins, S., Borle, A. and Stanko, R., Pyruvate prevents ischemia-reperfusion mucosal injury of rat small intestine. American Journal of Surgery 171:97–100; discussion 100–101, 1996.

Constantopoulos, G. and Barranger, J. A., Non-enzymatic decarboxylation of pyruvate, Analytical Biochemistry 139:353–358, 1984.

Crestanello, J. A., Lingle, D. M., Millili, J. and Whitman G. J., Pyruvate improves myocardial tolerance to reperfusion injury by acting as an antioxidant: a chemiluminescence study. Surgery 124:92–9, 1998.

DeBoer, L. W., Bekx, P. A., Han, L. and Steinke, L., Pyruvate enhances recovery of rat hearts after ischemia and reperfusion by preventing free radical generation. American Journal of Physiology 265:H1571–6, 1993.

Kuo, D. J., O'Connell, E. L. and Rose, I. A., Physical, chemical, and enzymological characterization of enolpyruvate. Journal of the American Chemical Society 101:5025–5030 1979.

Kurose, I., Argenbright, L. W., Wolf, R., Lianxi, L. and Granger, D. N., Ischemia/reperfusion-induced microvascular dysfunction: role of oxidants and lipid mediators. American Journal of Physiology 272:H2976–82, 1997.

Margolis, S. A. and Coxon, B., Identification and quantitation of the impurities in sodium pyruvate. Analytical Chemistry 58:2504–2510, 1986.

Muderawan, I. W., Bott, R. C., and Young, D. J., Chelation controlled addition of ethyl pyruvate to cyclic allylic stannanes. A diastereospecific route to functionalized bicyclic gamma-lactones. Synthesis 1640–1644, 1998.

O'Donnell-Tormey, J., Nathan, C. F. Lanks, K., DeBoer, C. J. and de la Harpe, J., Secretion of pyruvate. An antioxidant defense of mammalian cells. Journal of Experimental Medicine 165:500–14, 1987.

Peliska, J. A. and O'Leary, M. H., Preparation and properties of enolpyruvate. Journal of the American Chemical Society 113:1841–1842, 1991.

Perera, A., Parkes, H. G., Herz, H., Haycock, P., Blake, D. R., and Grootveld, M. C., High resolution NMR investigations of the reactivities of alpha-keto acid anions with hydrogen. Free Radical Research 26:145–57, 1997.

Salahudeen, A. K., Clark, E. C. and Nath, K. A., Hydrogen peroxide-induced renal injury. A protective role for pyruvate in vitro and in vivo. Journal of Clinical Investigation 88:1886–93, 1991.

Simpson, P. J. and Lucchesi, B. R., Free radicals and myocardial ischemia and reperfusion injury. Journal of Laboratory & Clinical Medicine 110:13–30, 1987.

Sawyer, D. T., Stamp, J. J. and Menton, K. A., Reactivity of superoxide ion with ethyl pyruvate, ($\alpha$-diketones, and benzil in dimethylformamide, Journal of Organic Chemistry 48:3733–3736, 1983.

Sekine, M., Futatsugi, T., Yamada, K. and Hata, T., A convenient synthesis of phosphoenolpyruvate via a silylester intermediate. Tetrahedron Letters 21:371–372, 1980.

Starostin, E. K., Radyukin, Y. N., Ignatenko, A. V. and Nikishin, G. I., Decomposition of the peroxides of the esters of keto acids by Fe(II) salts. Bulletin of the Academy of Sciences, USSR, Chemical Sciences 29:109–112, 1980.

Varma, S. D., Devamanoharan, P. S. and Ali, A. H., Prevention of intracellular oxidative stress to lens by pyruvate and its ester. Free Radical Research 28:131–5, 1998.

Vogt, J. A., Yarmush, D. M., Yu, Y.-M., Zupke, C., Fischrnan, A. J., Tompkins, R. G. and Buke, J. F., TCA cycle flux estimates from NMR— and GC-MS-determined 13C-glutamate isotopomers in liver. American Journal of Physiology 272: c2049–C2062, 1997.

Wattanasirichaigoon, S., Menconi, M. J., Delude, R. L. and Fink, M. P., Lisofylline ameliorates intestinal mucosal barrier dysfunction caused by ischemia and ischemia/reperfusion. Shock 11:269–75, 1999.

Yamazaki, H. and Shimada, T., Progesterone and testosterone hydroxylation by cytochromes P450, 2C19, 2C9, and 3A4 in human liver microsomes. Archives of Biochemistry a nd Biophysics 346:161–9, 1997.

Yu, X., Alpert, N. M. and Lewandowski, E. D., Modeling enrichment kine tics from dynamic $^{13}$C-NMR spectra: theoretical analysis and practical considerations. American Journal of Physiology 272: C2037–C2048, 1997:

While the invention has been described in conjunction with specific embodiments thereof, it is evident that many alternatives, modifications, and variations will be apparent to those skilled in the art in light of the foregoing description. Accordingly, it is intended that the invention shall be directed to all such alternatives, modifications and variations as fall within the spirit and broad scope of the appended claims.

What is claimed is:

1. A method for treating a mammal suffering from ischemia or reperfusion injury, comprising administering to said mammal a therapeutically effective amount of a composition consisting essentially of an ester of a 2 ketoalkanoic acid selected from the group consisting of ethyl pyruvate, propyl pyruvate butyl pyruvate, carboxymethyl pyruvate, acetoxymethyl pyruvate, carbethoxymethyl pyruvate and ethoxymethyl pyruvate in a pharmaceutically-acceptable carrier, wherein said carrier further comprises an organic or inorganic cation.

2. The method of claim 1, wherein said pharmaceutically-acceptable carrier is a Ringer's solution of isotonic saline supplemented with potassium ion.

3. The method of claim 1, wherein said 2-ketoalkanoic acid ester is admixed in a saline solution, said solution containing a cation selected from the group consisting of calcium and magnesium.

4. The method of claim 1, wherein the condition characterized by ischemia is selected from the group consisting of mesenteric ischemia, mesenteric thrombus, mesenteric venous occlusion, aortic aneurism repair, coronary artery bypass and surgical treatment of arterial occlusion of limbs.

5. The method of claim 1, wherein said ester of 2-ketoalkanoic acid is ethyl pyruvate.

6. The method of claim 1, wherein said mammal is suffering from ischemia.

7. The method of claim 6, wherein said ischemia is due to an ischemic event selected from the group consisting myocardial infarction, cerebral infarction and intestinal infarction.

8. The method of claim 1, wherein said mammal is suffering from reperfusion injury.

9. A method for treating a mammal suffering from ischemia or reperfusion injury comprising administering to said mammal a therapeutically effective amount of a composition consisting essentially of an ester of a 2 ketoalkanoic acid selected from the group consisting of ethyl 2-ketobutyrate, ethyl 2-ketopentanoate, ethyl 2-keto-3-methyl-butyrate, ethyl 2-keto-4-methyl-pentanoate and ethyl 2 ketohexanoate in a pharmaceutically acceptable carrier wherein said carrier further comprises an organic or inorganic cation.

10. The method of claim 1, wherein said 2-ketoalkanoic acid ester is admixed in a saline solution, said solution containing a cation selected from the group consisting of calcium and magnesium.

* * * * *

UNITED STATES PATENT AND TRADEMARK OFFICE
CERTIFICATE OF CORRECTION

PATENT NO.    : 6,846,842 B2
DATED         : January 25, 2005
INVENTOR(S)   : Alfred M. Ajami, Carrie A. Sims and Mitchell P. Fink

It is certified that error appears in the above-identified patent and that said Letters Patent is hereby corrected as shown below:

Title page,
Item [73], Assignee, delete "Beth Israel Deconess Medical Center" and insert therefor -- Beth Israel Deaconess Medical Center --;

Column 16,
Line 5, delete "The method of claim 1" and insert therefor -- The method of claim 9 --.

Signed and Sealed this

Twenty-fourth Day of May, 2005

JON W. DUDAS
*Director of the United States Patent and Trademark Office*